United States Patent [19]

Daffer et al.

[11] Patent Number: 5,101,809
[45] Date of Patent: Apr. 7, 1992

[54] VIBRATORY SAUNA

[75] Inventors: Steven J. Daffer, Edina; Ernest J. DeLanghe, Minnetonka; William M. Turner, Excelsior, all of Minn.

[73] Assignee: Sybaritic, Inc., Minneapolis, Minn.

[21] Appl. No.: 508,774

[22] Filed: Apr. 13, 1990

[51] Int. Cl.$^5$ .............................................. A61H 1/00
[52] U.S. Cl. ........................................ 128/33; 128/52; 128/57; 128/373; 4/529
[58] Field of Search ............... 4/524, 529; 128/373, 128/376, 24.1, 33, 52, 57

[56] References Cited

U.S. PATENT DOCUMENTS

| | | | |
|---|---|---|---|
| 3,051,180 | 8/1962 | Adams-Ray et al. | 128/373 |
| 3,389,699 | 6/1968 | Mathers | 128/33 |
| 3,405,709 | 10/1968 | Mathers | 128/33 |
| 3,882,856 | 5/1975 | Heuser et al. | 128/57 |
| 4,565,188 | 1/1986 | Hardie | 128/33 |
| 4,656,998 | 4/1987 | Masuda et al. | 128/52 X |
| 4,671,284 | 6/1987 | Wilson et al. | 128/373 |
| 4,712,538 | 12/1987 | Hardie et al. | 4/524 X |
| 4,884,574 | 12/1989 | Hardie et al. | 4/529 X |
| 4,886,051 | 12/1989 | White | 128/57 X |
| 4,947,833 | 8/1990 | Yamasaki | 128/52 |

FOREIGN PATENT DOCUMENTS

182398 11/1962 Sweden .

Primary Examiner—Robert A. Hafer
Assistant Examiner—Brian E. Hanlon
Attorney, Agent, or Firm—Kinney & Lange

[57] ABSTRACT

A personalized sauna comprising an elongated, horizontally extending bed which is connected to a supporting pedestal. The bed is positioned at least partially within the pedestal and is designed to an individual in a horizontal position. The sauna also includes a structure for uniformly directing downwardly heated, recirculating air above and over the top of the bed to provide an air shower and a flow of air over a person lying on the bed. The structure includes a cover member, hingedly mounted to the pedestal at the end which extends substantially along the entire length of the bed. An elongated upper chamber is formed within the cover member and extends substantially along the entire length of the cover member. A duct is formed on the cover and has air outlet openings leading from the duct to the chamber for introducing recirculated air into the chamber. A blower is supported on the cover for circulating air from the chamber, which enters through air inlet openings, into the duct. A heating element is provided within the duct for heating the air. The air outlets are spaced substantially along the entire length of the duct and upper chamber for downwardly distributing air heated by the elements from the duct into the chamber and thus, above and over the individual's body lying atop the bed with a generally uniform air flow rate along the length of the body.

29 Claims, 5 Drawing Sheets

VIBRATORY SAUNA

BACKGROUND OF THE INVENTION

The invention relates to a personal vibratory air-shower sauna, and in particular, it relates to an enclosure in which an individual can be positioned horizontally and provided with a flow of heated air over the body by an overhead downwardly directed air shower while being vibrated in a totally enclosed cabinet, except for the individual's head.

The combination of using vibration and heat therapeutic value is well know. Generally, blood flow is increased to areas stimulated by vibration, which in turn induces relaxation and facilitates transport of body waste materials for elimination from the body. It has been theorized that muscles that are not utilized in everyday life will remain healthy and supple with the utilization of vibration therapy.

Heating the skin to induce sweating has been known to enlarge pores of the skin and allow body waste products to leave the body. In addition to cleansing the outer skin layers by perspiration, heat also increases blood flow by dilating blood vessels. Increased circulation of blood accelerates blood flow to internal organs thereby assisting in processing and transporting body waste materials. Beautiful skin and a healthy, toned body are common results to the dry heat provided by a sauna.

The Hardie U.S. Pat. No. 4,565,188 and the Wilson et al. U.S. Pat. No. 4,671,284 show personal saunas with vibratory features. The Hardie patent describes a vibratory sauna which includes a housing having a chamber located below the support member. A heater is located in the lower chamber. Heated air flows out of the chamber and above the support member (over the body of a user) while the support member is being vibrated.

The Wilson et al. patent describes a sauna with a bed and a chamber beneath the bed with longitudinally extending heating elements within the chamber. The sauna includes elongated air inlets which extend substantially the entire length of the heating elements. In addition, elongated air outlets are included which also extend substantially along the entire length of the bed and direct air from beneath the bed surrounding the body and recirculating the same to the chamber beneath the bed by means of the air inlets.

SUMMARY OF THE INVENTION

A personalized vibratory air-shower sauna comprising an elongated, horizontally extending bed which is connected to a supporting pedestal. The bed is positioned at least partially within the pedestal and is designed to an individual lying in a horizontal position.

The air-shower sauna also includes a structure for uniformly directing heated, recirculating air from above the bed downwardly and over the top of the bed to provide a flow of air over a person lying on the bed. The structure includes a cover member, hingedly mounted to the pedestal at the end which extends substantially along the entire length of the bed. An elongated upper chamber is formed within the cover member and extends substantially along the entire length of the cover member. A duct is formed on the cover and has air outlet openings leading from the duct to the chamber for introducing recirculated air into the chamber. A blower is supported on the cover for circulating air from the chamber, which enters through air inlet openings, into the duct. A heating element is provided within the duct for heating the air. The air outlets are spaced substantially along the entire length of the duct and upper chamber for distributing air heated by the elements from the duct into the chamber from above and thus, downwardly and over the individual's body lying atop the bed with a generally uniform air flow rate along the length of the body.

In a preferred embodiment, a vibration mechanism is disposed beneath the bed and coupled to the bed for vibrating the bed. In an alternative embodiment, a roller for rolling under the back area of the individual to massage and relax the individual. In addition, a separate duct and fan system is provided for uniformly directing cool, fresh air to the head portion of an individual's body lying atop the bed.

DETAILED DESCRIPTION OF THE PREFERRED EMBODIMENTS

Figure 1:
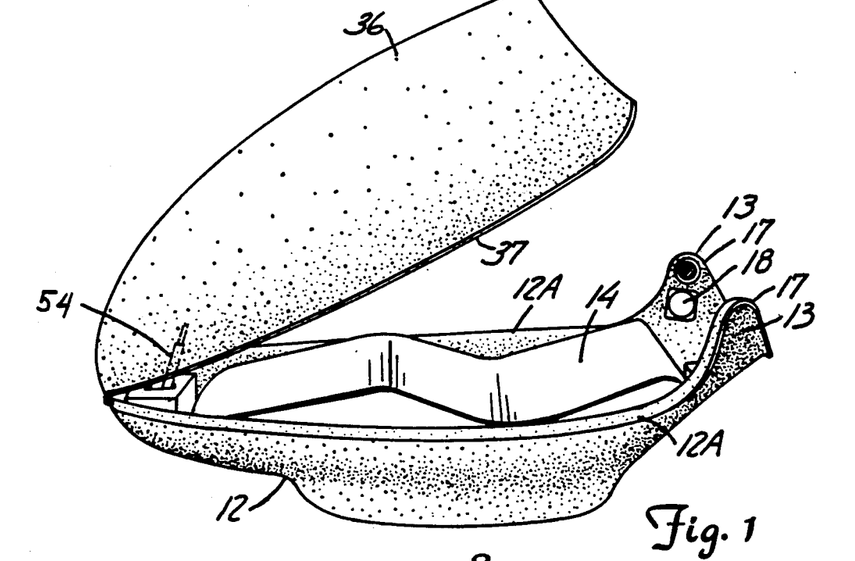
FIG. 1 is a perspective view of the personalized vibratory air-shower sauna of the present invention with the cover member in a raised position.
Figure 4:
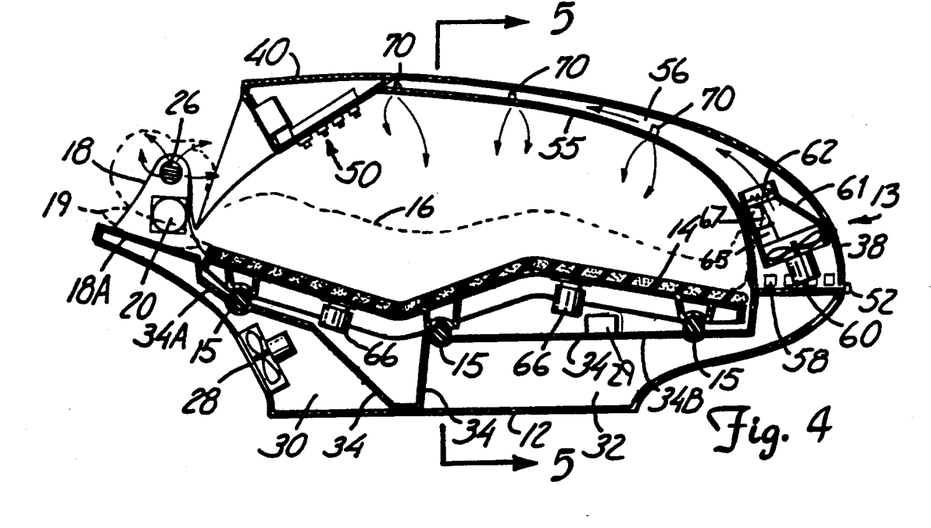
FIG. 4 is a side sectional view of an alternative embodiment of the personalized vibratory air-shower sauna of the present invention.
Figure 5:
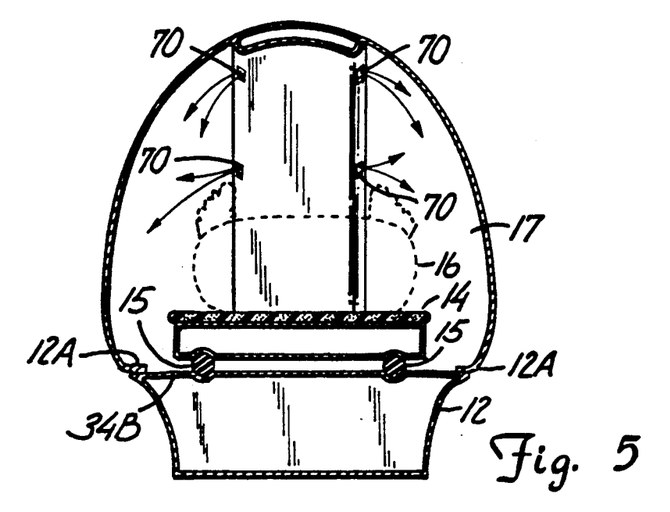
FIG. 5 is a sectional view of an alternative embodiment of the personalized vibratory air-shower sauna of the present invention taken along line 5—5 of FIG. 4.

The personal vibratory air-shower sauna of the present invention is generally indicated at 10 in FIGS. 1 and 4. The sauna 10 includes a supporting pedestal 12 and a blower-duct system 13 for uniformly directing heated, recirculating air downwardly and over a person in the sauna.

The pedestal 12 supports a bed 14 for supporting an individual 16 in a horizontal position. The bed 14 will support all of the body but the head in a body compartment 17. The bed 14 is constructed of known materials and is situated on top of the pedestal 12 supported by a plurality of resilient supports 15. In addition, the bed 14 is elongated and horizontally extending such that the bed 14 is positioned at least partially within the pedestal 12. As shown, the upper surface can be contoured for comfortable support of a user's body. By contouring the bed 14, no pressure points exist on the individual 16 and vibration is evenly distributed over the individual's entire body.

The pedestal 12 further includes a pair of spaced upright, somewhat outwardly inclined hollow wing members 18 at the head end of the pedestal. The pedestal 12 has a support wall section 18A that extends between the hollow wing members 18. The wall 18A supports a pillow 19 which provides support for the head of the individual 16 on the top of the bed 14. The wing members 18 extend to a height approximately equal to the front of the face of the individual 16 when the individual 16 is lying in a supine position as shown.

The wing members 18 have double panels and have inner panels 22 which have speakers 24 mounted on support screens 20. Each of the speakers 24 is positioned to be in an adjacent relationship to the ears of the individual 16. The speakers 24 provide stereo music or other sounds to further enhance the pleasurable experience during use of the sauna 10.

The inner panels 22 of the wing members 18 further include fresh air vents 26 for uniformly directing cool fresh air to the head portion of the individual lying atop the bed. The fresh air is directed through the vents 26 by a cooling fan 28 which blows cool air into the hollow wing members 18 and out the vents 26 as will be described in detail later in this disclosure.

In addition, the pedestal 12 includes a first hollow portion or cavity 30 and a second hollow portion or cavity 32. The first hollow portion 30 and the second hollow portion 32 are separated by wall members 34. The wall members 34 form an air-tight seal between the first hollow portion 30 and the second hollow portion 32.

Figure 2:
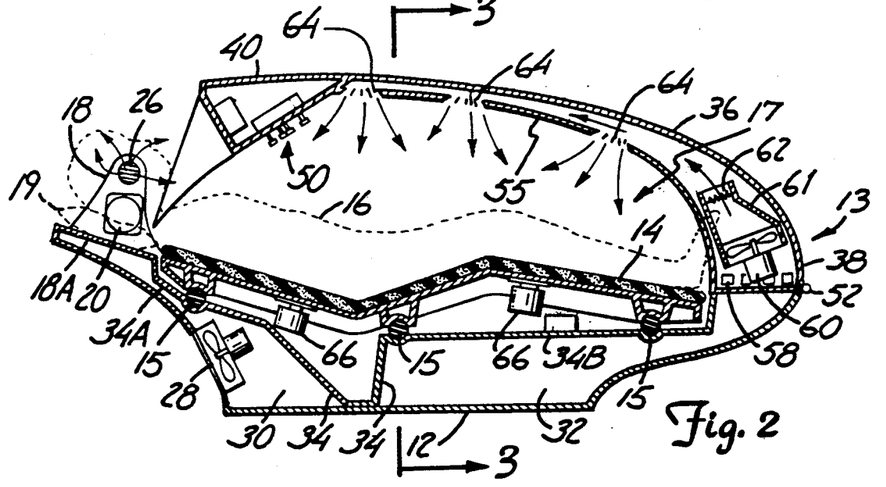
FIG. 2 is a side sectional view of the personalized vibratory air-shower sauna of the present invention.

The first hollow portion 30 includes the cooling fan 28 for circulation of fresh air to the face of an individual 16 lying in the sauna 10 as best illustrated in FIG. 2. The cooling fan 28 includes a fan housing connected to the pedestal 12 and draws air from outside the sauna 10 and into the first hollow portion 30. Thereafter, air is discharged through the ducts formed by the upper wall of the pedestal 18A and 34A and by the double-spaced walls of the wing member 18, and out through the air vents 26 onto the head of the individual 16, as indicated schematically by the arrows in FIG. 2.

The configuration of the wing members 18, in cooperation with the air discharged through the vents 26 by the fan 28, maintains a positive air pressure in the space adjacent the head of the individual 16 and provides an "air curtain" to generally preclude heated air discharging from the sauna 10 body compartment 17. Positive air pressure in the exterior region of the wing members 18 adjacent the individual's head increases efficiency of the sauna 10 by reducing the amount of heated air that would otherwise escape from the sauna 10.

Introduction of fresh air through the air vents 26 by the fan 28 also functions to provide a continuous supply of air to the head of the individual 16, for cooling the individual 16 and enabling breathing of fresh air which is not circulating within the sauna 10.

The blower-duct system 13 for uniformly downwardly directing heated, recirculating air is mounted on a cover member 36 having a foot end 38 and a head end 40 which defines the body compartment 17 for enclosing the major portion of an individual 16 lying on the bed 14 with the exception of the individual's head. The cover member 36 is hinged to the pedestal 12 at the foot end 38 and extends substantially along the entire length of the bed 14. The cover member 36 has side edges 37 which rest on side edges 12A of the pedestal when the cover is in a closed position. The cover has a head end seal panel 39 that is sealed to the cover and extends toward the bed. A head opening 42 is defined in the panel 39 at the head end 40 to the head of the individual 16 to extend out of compartment 17. The edges 37 and 12A, of the cover member 36 and the pedestal 12, have resilient seal materials for closing off air flow, and the head opening 42 also can be lined with a resilient gasket material.

In addition, a control panel 44 is also included on the cover member 36 located above panel 39 and the head opening 42 at the head end 40. The control panel 44 includes a stereo system 46 and readout instruments 48 which allow the individual 16 to view the level of the various environments present in the sauna 10, such as temperature, vibration, volume, and the like. Control knobs 50 are located under the cover member 36 to allow the individual 16 to freely adjust the various environments previously mentioned without having to raise the cover member 36.

The cover member 36 is hingedly attached to the pedestal 12 at the foot end 38 by a hinge mechanism 52 as best illustrated in FIGS. 1 and 2. Lifting the cover member 36 causes the cover member 36 to pivot on the hinge mechanism 52. A conventional gas-loaded spring 54 is attached to the pedestal 12 and the cover member 36 to assist the individual 16 in lifting the cover member 36 from a closed position.

Figure 3:
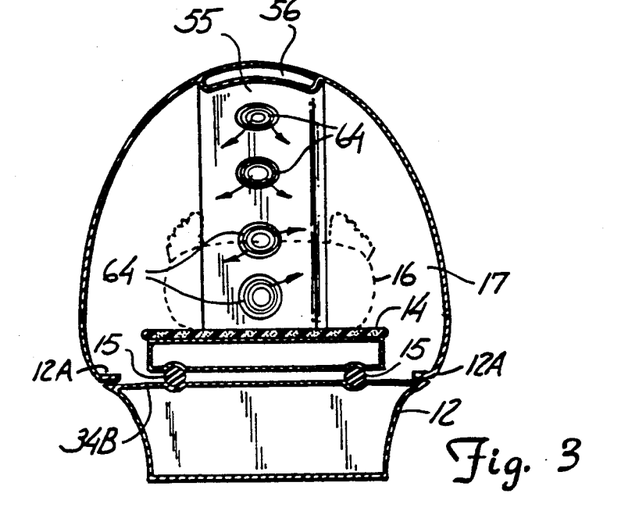
FIG. 3 is a sectional view of the personalized vibratory air-shower sauna of the present invention taken along line 3—3 of FIG. 2.

A channel-shaped duct wall 55 is attached to the inner surface of the top wall of the cover 36 and forms an elongated chamber 56. The duct chamber 56 extends substantially along the entire length of the cover member 36 as best illustrated in FIG. 2. (See FIG. 3 also).

The duct wall 55 has side wall portions that increase in height near the foot end of the cover, and a plurality of air inlets 58 are formed in the duct wall of the foot end 38. The inlets permit air flow from body chamber 17 to the above duct chamber 56 for introducing recirculated air into the duct chamber 56 when a fan or blower 60 is operating. The air inlets 58 are located at the foot end 38 of the cover member 36 and are preferably in the form of vents or slots. The location of the air inlets 58 at the foot end 38 of the cover member 36 facilitates the desired air flow patterns within the chamber 17 of sauna 10.

The blower or fan 60 is mounted on a housing 61 which is fixed to the duct walls 55 within the chamber 56 for driving the recirculated air introduced into the chamber 56 by way of the air inlets 58. The blower or fan 60 is preferably located at the foot end 15 of the cover member 36 such that as recirculated air is introduced into the chamber 56, the blower 60 blows the air through the chamber 56 and draws air in through the air inlets 58, as indicated schematically by the arrows in FIG. 2.

A heat duct 61 including a heating element 62 is provided within the chamber 56 for heating the recirculated air driven by the blower 60. The heating element 62 is situated such that after the air passes through the blower 60 and into duct 61, the air flows over the heating element 62 and is heated (if desired) before traveling further through the chamber 56.

The heat duct 61 also includes ozone 65 and ultraviolet 67 lamps. The ozone lamp 65 produces oxygen activated lamps which consume bacteria. The ultraviolet lamp 67 is used for sterilization and for purifying the recirculated air.

The air driven by the blower or fan 60 travels through the duct chamber 56, as illustrated schematically in FIG. 2 and passes out of the chamber through a plurality of spaced air outlets 64 in the side wall portions of the duct wall. The air outlets 64 are positioned along the entire length of the chamber 56. The air outlets 64 distribute the air heated by the heating element 62 and downwardly discharging from the duct chamber 56 to an individual's body 16 lying atop the bed 14 with a generally uniform air flow rate along the length of the individual's body. The air outlets 64 are preferably in the form of vents and can have deflector vane covers, if desired. In the preferred embodiment, the air outlets 64 are spaced equidistant from each other and direct the air toward the individual 16 by use of vanes. By locating the air outlets 64 in this manner, the air flows uniformly in an air shower above and around the individual's body as illustrated schematically in FIGS. 2 and 3. The uniform air flow prevents certain areas of the body of the individual 16 from receiving air which is either too hot or too cold. In addition, uniform air flow prevents an individual 16 from receiving air flow which has an unequal velocity. However, adjustable dampers can be used with the air outlets 64 for permitting individualized air flow patterns.

Figure 6:
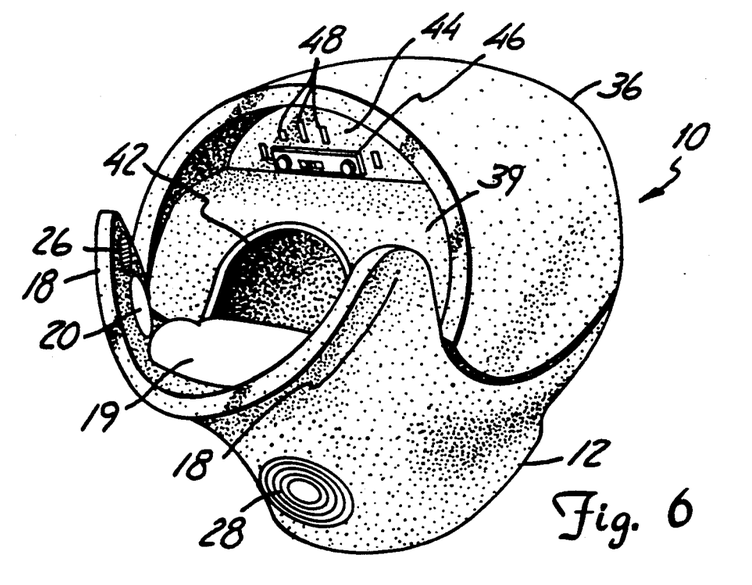
FIG. 6 is a perspective view of the personalized vibratory air-shower sauna of the present invention with the cover member in a closed position.
Figure 7:
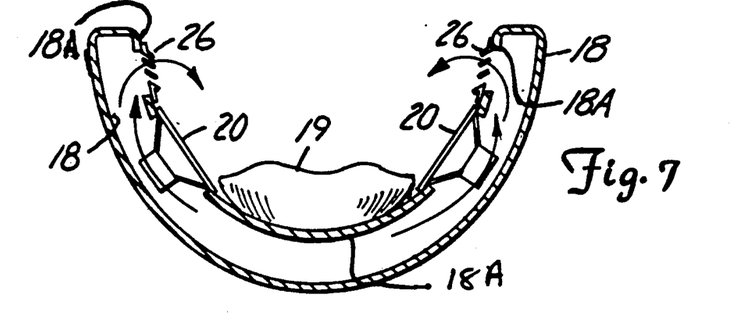
FIG. 7 is a sectional view of the hollow wing members.
Figure 8:
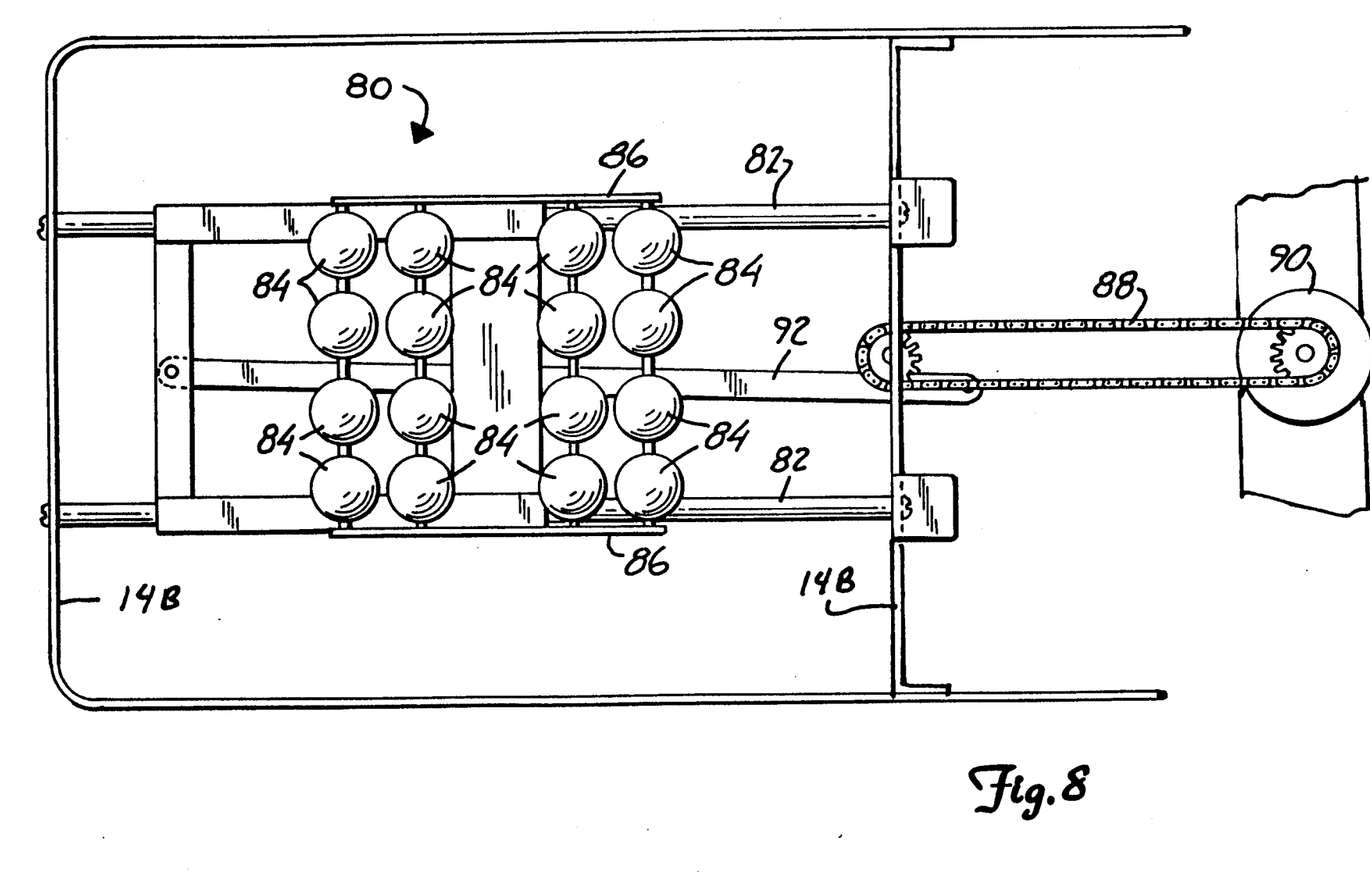
FIG. 8 is bottom view of the rollers of the present invention.

In another embodiment, as illustrated in FIGS. 6 and 7, a plurality of air outlets 70 are located equidistant from each other along either side of the duct wall 55. Adjustable dampers can be used with the air outlets 70 for permitting individualized air flow patterns.

The air outlets 64 and 70 also may serve to supply an aromatic scent to the individual 16, if the individual 16 so desires. An aroma (perfume or air freshener) dispenser pump 29 is situated below the bed and is disposed such that an individual 16 can activate the pump at selected times and the freshener will be sprayed into the chamber 56 and carried out over the individual 16 by way of the air outlets 64 and 70. The perfume or air freshener dispensed by the aroma pump 29 assists in masking any body odors which could be associated with the perspiration and sweating of the individual 16.

Preferably, at least one electric vibrator 66 is mounted to the bed 14 below it for vibrating the bed 14. As shown, two vibrators are shown. Each vibrator 66 is bolted to the underside of the bed 14 and is preferably in the form of a variable speed electric motor having eccentric weights attached thereto. Rotation of the weights by the motor causes vibration of the bed 14 on the resilient supports 15.

The resilient supports 15 are elastomer balls (spheres) set in part spherical receptacles on upper walls 34A and 34B in the pedestal and in the lower wall 14A of the bed. Other resilient mountings can be used. The hardness or stiffness of the resilient mountings can be selected to suit the weight of the user and the amount of vibration dampening desired.

The vibrator 66 provides a general vibration which has a soothing and relaxing effect on the individual 16 using the sauna The vibratory sauna 10 of the present invention is also useful in that the individual 16 may have tired muscles and wound up nerves relaxed in the general facade of essential vibration and passive heat combinations.

In another preferred embodiment, in addition to or in place of the vibrator 66, at least one roller 80, generally as the type that is shown in U.S. Pat. No. 3,389,699, is mounted on a frame 86 which in turn is slidably mounted to guide rails 82 beneath a pad on the bed 14 for rolling under the bed 14. The guide rails 82 are supported to frame members 14B of the pedestal 12. The support 14A for the bed is flexible enough to follow the contour of the rollers 80 and yet provide support for the individual 16. Several rollers 80 are shown, and each includes a plurality of resilient spheres 84 which are rotatably mounted on shafts supported on the frame 86.

The rollers 80 can be moved back and forth to roll under the back area of an individual 16 to massage and relax the individual 16. The frame 86 is driven by a chain 88 mounted over spaced sprockets, one of which is powered by a drive motor 90. A connecting link 92 is attached to one link of the chain 88 and the other end of connecting link 92 is connected to the frame 86 by conventional means such as spherical seat rod ends. The connecting link 92 links the chain 88 to the frame 86 such that the frame 86 reciprocates and the resilient individual spheres 84 can roll under the back of an individual 16. The rollers 80 can be adjusted to different heights which can be controlled by the individual 16 in order to achieve the desired amount of pressure on the back area of the individual 16. The frame 86 comprises a pair of sleeves mount on rails 82. The sleeves are held together by cross-members and resilient support frames 85 support the shaft of each roller 80 in a desired manner.

The cooling fan 28, the blower 60 and the motor 90 used to drive frame 86 are preferably variable speed and are controlled in order to allow the individual 16 to adjust the cooling fan 28 and the blower 60 and the roller action to the desired speed. In addition, the amount of heat produced by the heater 62 is adjustable to allow the individual 16 to set the heat at a level which is the most comfortable to the individual 16.

The vibrators 66, the motor 90, the fans 28 and 60 and the heater 62, all are powered through adjustable controls which are operated by the individual 16 using the sauna 10. The speed of the vibrators 66, motors 90 (and thus, rollers 80) and the fans 28 and 60 and power provided to the heater 62 can be controlled in a known manner.

Figure 9:
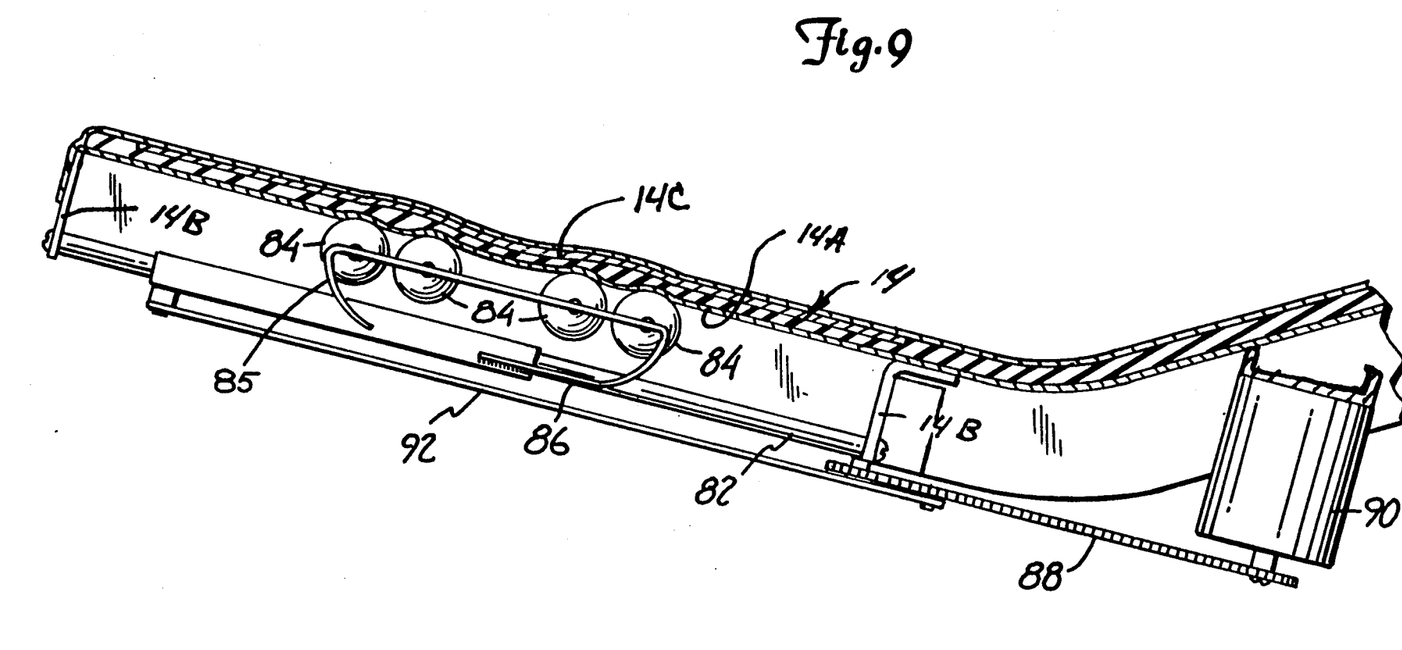
FIG. 9 is a side view of the rollers of the present invention.

Although the present invention has been described with reference to preferred embodiments, workers skilled in the art will recognize that changes may be made in form and detail without departing from the spirit and scope of the invention. An electric heating pad 14C is shown in FIG. 9 near the top of bed 14 and can be used with or without the roller system. It may be variably controlled for comfort and muscle relaxation. A high limit heater safety cutoff switch can be used in the duct system for preventing excessive temperatures.

What is claimed is:

1. An air-shower sauna having a supporting pedestal and an elongated, horizontally extending bed connected to the pedestal for supporting an individual in a horizontal position, the pedestal having side edges and the sauna including means for uniformly directing heated, downwardly directed recirculating air toward selected portions of an individual's body lying atop the bed, the means comprising:
    a cover member above the bed having side edges and extending substantially along the length of the bed to overlie the bed and provide a space for a person on the bed, the cover member being hingedly mounted to the pedestal;
    an elongated duct chamber formed on the interior of the cover member and extending substantially along the length of the cover member;
    air inlet means coupled to the duct chamber for introducing recirculated air from the space into the duct chamber;
    blower means mounted on the cover member for moving the recirculated air through the duct chamber; and air outlet openings spaced along the length of the duct chamber for distributing air from the duct chamber downwardly to an individual's body lying atop the bed above and along the length of the body as the air flows over and back toward the air inlet means.

2. The sauna of claim 1 wherein the bed is contoured.

3. The sauna of claim 1 and vibration means disposed beneath the bed and coupled to the bed for vibrating the bed.

4. The sauna of claim 1 and means separate from the duct chamber for directing cool, fresh air to the head portion of an individual's body lying atop the bed.

5. The sauna of claim 1 and heating means disposed within the chamber for heating the recirculated air moved by the blower means through the duct chamber.

6. The sauna of claim 1 wherein the heating means includes a heating element, the heating element disposed within a heat duct.

7. The sauna of claim 1 wherein the duct chamber is located substantially centrally in the cover member.

8. The sauna of claim 1 wherein the bed is positioned at least partially within the pedestal.

9. The sauna of claim 4 wherein the means include a pair of hollow wing members, the wing members extending along each side of the head portion of an individual lying atop the bed.

10. The sauna of claim 1 wherein the side edges of the pedestal and the side edges of the cover member will engage when the sauna is in a closed position.

11. The sauna of claim 1 and an aroma dispenser means for dispensing an aroma to an individual, the aroma dispenser means being located beneath the bed.

12. The sauna of claim 11 wherein the aroma dispenser means includes a pump, the pump being connected to the duct chamber whereby an aroma is dispensed through the air outlet openings.

13. The sauna of claim 1 and roller means for rolling under the back area of the individual to massage and relax the individual.

14. The sauna of claim 1 wherein the duct chamber includes an ozone lamp.

15. The sauna of claim 1 wherein the duct chamber includes an ultraviolet lamp.

16. An air-shower sauna having a supporting pedestal and an elongated, horizontally extending bed connected to the pedestal for supporting an individual in a horizontal position, and means for uniformly downwardly directing heated, recirculating air to portions of an individual's body lying atop the bed, the means comprising:
a cover member above the bed and extending substantially along the length of the bed, the cover member being hingedly mounted to the pedestal;
an elongated duct chamber formed within the cover member and extending substantially along the length of the cover member;
a plurality of air inlets coupled to the duct chamber for introducing recirculated air into the duct chamber;
blower means connected to the duct chamber and mounted on the cover for blowing the recirculated air through the duct chamber;
a heating element disposed within the duct chamber for heating the recirculated air; and
a plurality of air outlets spaced along the length of the duct chamber for distributing air heated by the heating element from the duct chamber downwardly and over an individual's body lying atop the bed with a generally uniform air-flow rate above and along the length of the body.

17. The sauna of claim 16 and vibration means disposed beneath the bed and coupled to the bed for vibrating the bed.

18. The sauna of claim 16 and means for uniformly directing cool, fresh air to the head portion of an individual's body lying atop the bed.

19. The sauna of claim 16 wherein the duct chamber is located substantially centrally in the cover member.

20. The sauna of claim 16 wherein the bed is positioned at least partially within the pedestal.

21. The sauna of claim 18 wherein the means include a pair of hollow wing members, the wing members extending along each side of the head portion of an individual lying atop the bed.

22. The sauna of claim 16 and an aroma dispenser means for dispensing an aroma to an individual, the aroma dispenser means being located beneath the bed.

23. The sauna of claim 22 wherein the aroma dispenser means includes a pump, the pump being connected to the duct chamber whereby an aroma is dispensed through the air outlet openings.

24. The sauna of claim 22 wherein the aroma includes perfume or air freshener.

25. The sauna of claim 16 and roller means for rolling under the back area of the individual to massage and relax the individual.

26. The sauna of claim 16 wherein the duct chamber includes an ozone lamp.

27. The sauna of claim 16 wherein the duct chamber includes an ultraviolet lamp.

28. The sauna of claim 1 and
roller means supported on the bed and positioned below a person lying on the bed; and
means operable to move the roller means along the bed to provide massaging action to a person on the bed.

29. The sauna of claim 28 wherein the means includes an elongated duct formed on the interior of the cover member with air outlet openings spaced along the length of the duct for distributing the air form the duct.

* * * * *

UNITED STATES PATENT AND TRADEMARK OFFICE
CERTIFICATE OF CORRECTION

PATENT NO.  : 5,101,809
DATED       : April 7, 1992
INVENTOR(S) : Steven J. Daffer, Ernest J. DeLanghe, William M. Turner It is certified that error appears in the above-identified patent and that said Letters Patent is hereby corrected as shown below:

Col. 8, line 52, after "provide", insert "a"

Col. 8, line 57, delete "form", insert "from"

Signed and Sealed this

Twenty-fifth Day of May, 1993

Attest:

MICHAEL K. KIRK

Attesting Officer

Acting Commissioner of Patents and Trademarks